United States Patent [19]

Wood

[11] Patent Number: 4,510,134

[45] Date of Patent: Apr. 9, 1985

[54] CONTROLLING NEMATODES IN ANIMALS AND SOIL WITH NEMATOCIDAL ANTIBIOTICS

[75] Inventor: Irwin B. Wood, Pennington, N.J.

[73] Assignee: American Cyanamid Co., Stamford, Conn.

[21] Appl. No.: 376,046

[22] Filed: May 7, 1982

[51] Int. Cl.³ .................. A61K 31/71; A61K 31/70; A61K 35/74; A61K 31/35

[52] U.S. Cl. .................................... 514/27; 424/114

[58] Field of Search ............... 424/180, 181, 283, 114

[56] References Cited

U.S. PATENT DOCUMENTS 4,278,663  7/1981  Liu et al. .............................. 424/180

Primary Examiner—Jerome D. Goldberg
Attorney, Agent, or Firm—H. G. Jackson

[57] ABSTRACT

There is provided a method for controlling nematodes in warm-blooded animals by orally administering thereto a nematocidally effective amount of a new antibiotic or mixture of antibiotics produced in a microbiological fermentation under controlled conditions using a newly discovered strain of *Actinomadura yumaense* and mutants thereof.

There is also provided a method for controlling nematodes in soil by applying to said soil a nematocidally effective amount of the above-mentioned antibiotic or antibiotic mixture.

8 Claims, No Drawings

CONTROLLING NEMATODES IN ANIMALS AND SOIL WITH NEMATOCIDAL ANTIBIOTICS

The present invention relates to a method of preventing, controlling, or treating nematode infestations in warm-blooded animals by orally administering thereto a nematocidally effective amount of an antibiotic selected from:

X 14868A, having the postulated structure:

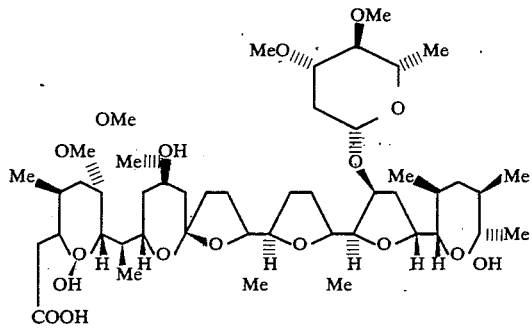

and LL-C23024β, having the postulated structure:

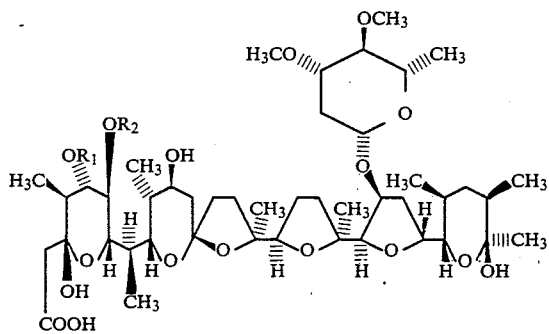

wherein
$R_1$=H or $CH_3$
$R_2$=H or $CH_3$
and $R_1$—does not equal $R_2$
pharmaceutically acceptable salts of the compounds, mixtures thereof, or fermentation broths or harvest mash solids from which said nematocidal antibiotics are obtained.

This invention also relates to a method for controlling nematodes in soil by applying to the soil a nematocidally effective amount of an antibiotic X 14868A or LL-C23024β or pharmaceutically acceptable salts of said compounds, mixtures thereof, or fermentation broths or harvest mash solids from which said nematocidal antibiotics are obtained.

The antibiotics which are useful in the methods and compositions of this invention are antibiotics X 14868A and LL-C23024β. The LL-C23024β, and a method for the preparation thereof, are described in the U.S. patent application of John Henry Edward James Martin, et al., Ser. No. 313,849, filed concurrently herewith and incorporated by reference thereto.

U.S. application Ser. No. 116,696 (filed Jan. 30, 1981, now U.S. Pat. No. 4,278,663, assigned to Hoffman-LaRoche Inc. of Nutley, N.J.) discloses antibiotics X-14868A and X-14868B having the formulas:

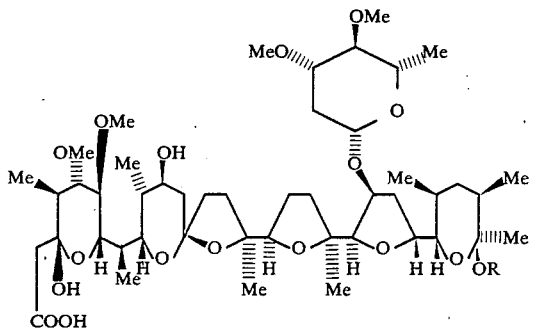

X-14868A: R=H
X-14868B: R=Me

The invention, as it applies to the control of nematodes in warm-blooded animals, involves the oral introduction into said animals of a nematocidal, antibiotic composition comprising an edible carrier or drinking water containing about 0.5 ppm to 30 ppm, and preferably 1.0 ppm to 15 ppm, of an antibiotic X 14868A or LL-C23024β or pharmaceutically acceptable salts of said compounds and mixtures thereof, or fermentation broths or harvest mash solids containing the compounds.

The above-mentioned method and compositions are effective against both the adult and larval stages of a variety of nematode species that infest companion, farm, and laboratory animals. As such, the compositions of the invention are useful for the therapeutic treatment of animals such as dogs, cats, sheep, goats, horses, cattle, swine, poultry, rats, mice, and the like. The compositions of the invention are especially useful for treating nematode-infested companion and farm animals. However, they are also useful for treating rats and mice which are used as laboratory specimens and must be free of nematode infestations when employed for biological evaluations.

When using the compounds of the invention for the prevention or control of nematodes in animals, the active nematocidal agent is generally first prepared as an animal feed premix. These premixes usually contain a relatively high percentage of the nematocidal agent and are generally blended with the animal's feed either directly or after an intermediate processing step. If desired, the feed premix may also be applied as a top dressing for the animal's daily ration.

Feed premixes or concentrates, useful in the practice of the invention, may be prepared by admixing about 0.1% to 6% by weight of one of the above-identified antibiotics, pharmaceutically acceptable salt thereof, a mixture of said antibiotics, fermentation broths, or fermentation mash insolubles containing the same, with about 99.9% to 94% by weight of a suitable carrier or diluent.

Carriers suitable for use to make up the feed supplement compositions include the following: alfalfa meal, soybean meal, cottonseed oil meal, linseed oil meal, sodium chloride, corn meal, molasses, urea, bone meal, corncob meal, and the like. The carrier promotes a uniform distribution of the active ingredient in the finished feed into which the supplement is blended. It thus performs an important function by ensuring proper distribution of the active ingredient, i.e., about 0.5 to 30 ppm thereof throughout the feed. This is equivalent to 0.00005% to 0.003% by weight of active ingredient in the feed.

Continuous release and/or prolonged treatment boluses, useful in the practice of the invention for the treatment of ruminant animals, may be prepared by mixing 500 mg to 5,000 mg of X 14868A or LL-C23024$\beta$ with high specific density substances such as iron filing heavy metal salts, etc., and various resin polymers and of sufficient size to remain in the rumen for long periods of time such as one to five months. A resultant admixture may be then coated with a suitable substance such as ethylcellulose or various polymers to regulate the release of compound into the lumen of the rumen to control the helminth parasites.

Although administration of the compounds for control of nematodes in animals will generally be most practical in or with the feed, or in the drinking water, the compounds may also be administered to individual hosts in the form of tablets, drenches, capsules, sustained release boluses, or the like. These latter methods of administration are, of course, less practical for treatment of large groups of animals than they are for treating limited numbers of animals, but they are quite practical for use on a small scale or on an individual basis.

It is anticipated that the compositions of this invention will be effective for controlling a wide variety of nematodes in companion and farm animals; for example, it is expected that the compositions will be effective for controlling *Ancylostoma caninum, Ancylostoma braziliense, Ascaris suum, Oesophagostomum columbianum, Trichostrongylus colubriformis, Trichostrongylus axei, Trichostrongylus aceti, Haemonchus contortus, Ostertagia circumcenta,* and the like.

Since X 14868A and LL-C23034$\beta$ are relatively insoluble in water, it is generally desirable, when administering the compounds in the animal's drinking water, to dissolve the active compound in an organic solvent such as methanol, ethanol, acetone, or the like, and admix with said solution a small amount of surfactant and/or dispersing agent to assure solution and/or dispersion of the active ingredient in the animal's drinking water.

When the compositions of the invention are used for the control of nematodes in soil, the compositions are generally employed in dilute, solid, or liquid concentrations applied to the soil in sufficient quantity to provide about 0.125 kg/ha to 4.0 kg/ha, and preferably about 0.25 kg/ha to 3.0 kg/ha, of the nematocidal antibiotic.

It is preferred, therefore, to incorporate the antibiotics or antibiotic mixtures in a variety of suitable solid or liquid diluents. Such compositions can be prepared as dusts, granular formulations, emulsifiable concentrates, wettable powders, or the like.

When it is desirable to apply the active nematocidal composition as a dilute liquid, the emulsifiable concentrate or wettable powder is generally mixed with water or other inexpensive liquid diluent just prior to application and applied as a dilute aqueous suspension.

A typical emulsifiable concentrate can be prepared by dissolving about 5% to 25% by weight of the active ingredient in about 65% to 90% by weight of N-methylpyrrolidone, isophorone, butyl cellosolve, methanol, DMSO, or the like, and dispersing therein about 5% to 10% by weight of a nonionic surfactant such as an alkylphenoxy polyethoxy alcohol. This concentrate is dispersed in water for application as a liquid spray.

Wettable powders can be prepared by grinding together about 20% to 45% by weight of a finely divided carrier such as kaolin, bentonite, diatomaceous earth, attapulgite, or the like, 45% to 80% by weight of the active compound, 2% to 5% by weight of a dispersing agent such as sodium lignosulfonate, and 2% to 5% by weight of a nonionic surfactant, such as octylphenoxy polyethoxy ethanol, nonylphenoxy polyethoxy ethanol, or the like.

Dusts can be prepared in the same manner as wettable powders excepting that the dispersing agent and surfactant may be omitted.

Preparation of the granular product can be achieved by dissolving the active compound in a solvent such as acetone, methyl alcohol, or the like, and spraying the thus-prepared solution on a granular carrier such as corncob grits, sand, attapulgite, kaolin, or the like.

As indicated above, application of the compositions of the invention can be achieved with conventional dusting equipment, mechanical spreaders, and/or sprayers. The formulated compositions can be incorporated into the soil before planting or deposited in the furrow at planting time. Further, the aqueous suspension of the active ingredient can be applied as a drench to turf grass or in irrigation water; and, with a suitable carrier, can be injected into soil about the roots of established plants without phytotoxicity.

The above-described compositions and formulations are effective for controlling the root-knot nematode (*Meloidogyne* sp.) in soil.

The nematocidal agents of the present invention are designated X 14868A and LL-C23024$\beta$.

Antibiotics X 14868A and LL-C23024$\beta$ are organic carboxylic acids and thus are capable of forming salts with non-toxic pharmaceutically acceptable cations. Thus, salts formed by admixture of the antibiotic free acid with stoichiometric amounts of cations, suitably in a neutral solvent, may be formed with cations such as sodium, potassium, calcium, magnesium and ammonium, as well as organic amine cations such as tri(lower alkyl) amine (e.g. triethylamine, triethanolamine), procaine and the like. The cationic salts of antibiotics X 14868A and LL-C23024$\beta$ are, in general, crystalline solids, relatively insoluble in water and soluble in most common organic solvents such as methanol, ethyl acetate, acetone, chloroform, heptane, ether and benzene.

The new nematocidal agents X 14868A and LL-C23024$\beta$ are formed during the cultivation under controlled conditions of a new strain of *Actinomadura yumaense* sp. nov.

This new antibiotic producing strain was isolated from a soil sample collected in Yuma County, Arizona and is maintained in the culture collection of the Lederle Laboratories Division, American Cyanamid Company, Pearl River, N.Y. as culture number LL-C23024. A viable culture of this new representative strain has been deposited with the Culture Collection Laboratory, Northern Utilization Research and Development Division, U.S. Department of Agriculture, Peoria, Ill., and has been added to its permanent collection under its accession number NRRL 12515.

Taxonomic Characterization of NRRL 12515

The strain NRRL 12515 has been taxonomically characterized and identified as the type strain of a new species of the genus Actinomadura to be known as *Actinomadura yumaense* sp. nov.

Observations were made of the cultural, physiological and morphological features of representative strain NRRL 12515 using methods detailed by E. B. Shirling and D. Gottlieb, "Methods for characterization of Streptomyces species", Internat. J. Syst. Bacteriol. 16: 313–340 (1966), and R. E. Gordon et al., "*Nocardia coeliaca, Nocardia autotrophica,* and the nocardin strain," Internat. J. Syst. Bacteriol. 24:54–63 (1974). Media used in this study were selected from those recommended by T. G. Pridham et al., "A selection of media for maintenance and taxonomic study of Streptomycetes," Antibiotics Ann., pp. 947–953 (1956/1957); G. F. Gauze et al., "Problems in the classification of antagonistic actinomycetes," State Publishing House for Medical Literature, Medgiz, Moscow (1957); and R. E. Gordon et al., supra, for the taxonomic study of actinomycetes and soil bacteria. Chemical composition of the cell walls of the microorganism was determined using the method of H. A. Leachevalier et al., "Chemical composition as a criterion in the classification of actinomycetes," Adv. Appl. Microbiol. 14:47–72 (1971). Phospholipid patterns were determined using the method of M. P. Lechevalier et al., "Chemotaxonomy of aerobic actinomycetes: phopholipid composition," Biochem. Syst. Ecol. 5:249–260 (1977). Details are recorded in Tables IV–IX, and a general description of the culture is given below. Underscored descriptive colors are taken from K. L. Kelly and D. B. Judd, "Color. Universal Language and Dictionary of Names," U.S. Nat. Bur. Stand., Spec. Publ. 440, Washington, D.C. (1(&6) and the accompanying Inter-Society Color Council, Natl. Bur. Stand. Centroid Color Charts.

The data observed for this novel species as represented by strain NRRL 12515 were compared with the data published for the known species of the genus Actinomadura [M. Goodfellow et al., "Numerical Taxonomy of Actinomadura and related actinomycetes," J. Gen. Microbiol. 122:95–111 (1979); L. H. Huang, "*Actinomadura macra* sp. nov., the producer of antibiotic CP-47,433 and CP-47,434," Internat. J. Syst. Bacteriol. 30:565–568 (1980); J. Meyer, "New species of the genus Actinomadura," Z. Allgem. Mikrobiol. 19:37–44 (1979); H. Nomura and Y. Ohara, "Distribution of actinomycetes in soil. XI. Some new species of the genus Actinomadura, Lechevalier, et al.," J. Ferment. Technol. 49:904–912 (1971); and T. P. Preobrazhenskaya et al., "Key for identification of the species of the genus Actinomadura," The biology of Actinomycetes and Related Organisms 12:30–38 (1977)]. Culture NRRL 12515 bears a slight resemblance to *Actinomadura pelletieri,* but resembles no other described species and differs from *A. pelletieri* in a number of characteristics. Therefore, strain NRRL 12515 has been designated the type strain of a new species to be known as *Actinomadura yumaense,* sp. nov., named for the site of collection of the soil sample from which the type strain was isolated.

Micromorphology

Spores are formed in short spiral chains (maximum length approximately 20 spores per chain) on branched, almost verticillate aerial sporophores. The spores are ovoid, 0.6 to 0.8 micron by 1.0 to 1.4 micron, with a smooth surface.

Cell Wall Composition

Whole cell hydrolysates of this culture contain madurose (3-O-methyl-D-galactose) and the meso isomer of diaminopimelic acid (DAP). The culture also has a Type P-1 phospholipid pattern and no other diagnostic phospholipid other than some phosphatidyl glycerol. These characteristics are all very typical of members of the genus Actinomadura.

Amount of Growth

Good growth is observed on Bennett's agar, Gauze No. 2 agar, NZ-amine-starch-glucose agar (ATCC medium 172), tomato paste-oatmeal agar, and yeast extract-malt extract agar; moderate growth is observed on Benedict's agar, Czapek's sucrose agar, glycerol-asparagine agar, Hickey-Tresner agar, and oatmeal agar; poor growth is observed on calcium malate agar, Gauze No. 1 agar, and inorganic salts-starch agar.

Vegetative Mycelium

On media where good growth occurred, the vegetative mycelium was observed to be raised and convoluted and was generally yellowish-gray shades in color.

Aerial Mycelium and Spore Color

Aerial mycelia and/or spore masses were white to 264. light gray in color. Aerial mycelia production is light on most media.

Soluble Pigments

Absent on many media; yellow pigment on Benedict's and glycerol-asparagine agars; yellow-green pigment on calcium malate agar; greenish brown pigment on NZ-amine-starch-glucose agar; orange pigment on Bennett's and yeast extract-malt extract agars.

Physiological Reactions

No melanin pigments on peptone-iron agar and tyrosine agar (ISO-7); strong peptonization of litmus milk; strong proteolysis of nutrient gelatin; moderate reduction of natrate; no hydrolysis of adenine or guanine; strong hydrolysis of hypoxanthine, tyrosine, and xanthine; weak hydrolysis of starch; hydrolysis of esculin; variable hydrolysis of urea. No growth at 4° C., 10°., or 55° C.; moderate growth at 25° C. and 45° C.; good growth at 32° C. and 37° C. Carbohydrate utilization as per the method of T. G. Pridham and D. Gottlieb, "The utilization of carbon compounds by some actinomycetales as an aid for species determination," J. Bacteriol. 56:107–114 (1948): good utilization of glucose, glycerol and trehalose; moderate utilization of maltose and sucrose; poor utilization of fructose, galactose, inositol, mannose, and melezitose; no utilization of adonitol, arabinose, dulcitol, lactose, mannitol, melibiose, raffinose, rhamnose, salicin, sorbitol and xylose. Acid production from carbohydrates by the method of Gordon, et al., supra: Good acid production from glucose, glycerol, maltose, sucrose and trehalose; weak acid production from galactose, inositol and mannose. Utilization of organic acids by the method of Gordon et al., supra: utilization of acetate, malate, propionate, pyruvate, succinate and tartrate; no utilization of benzoate, citrate, lactate, mucate and oxalate.

TABLE I

Cultural Characteristics of *Actinomadura yumaense* NRRL 12515

Incubation: 14 days  Temperature: 28° C.

| Medium | Amount of Growth | Aerial Mycelium and/or Spores | Soluble Pigment | Reverse Color |
|---|---|---|---|---|
| Benedict's Agar | Moderate to poor | Flat, powdery colonies; aerial mycelia white to 264. light gray | Yellowish | 89. pale yellow |
| Bennett's Agar | Good | No aerial mycelia; convoluted vegetative growth 93. yellowish gray to 80. grayish yellowish brown | Orange | 81. dark grayish yellowish brown |
| Calcium Malate Agar | Poor | Flat growth; sparse white aerial mycelia | Yellow-green | 90. greenish yellow |
| Czapek's Sucrose Agar | Poor to Moderate | Flat growth; moderate aerial mycelia vegetative growth 90. grayish yellow | None | 89. pale yellow |
| Gauze No. 1 Agar | Poor | Colorless flat growth; sparse white aerial mycelia | None | Colorless |
| Gauze No. 2 Agar | Good | Raised convoluted colonies; vegetative mycelia 93. yellowish gray; moderate aerial mycelia, 92. yellowish white | None | 72. dark orange yellow |
| Glycerol-Asparagine Agar | Poor to Moderate | Flat, powdery colonies; white aerial mycelia | Yellow | 89. pale yellow |
| Hickey-Tresner Agar | Moderate | Flat waxy colonies, 90. grayish yellow sparse aerial mycelia, white to 264. light gray | None | 90. grayish yellow |
| Inorganic Salts-Starch Agar | Poor | Flat, colorless, powdery colonies; white aerial mycelia | None | Colorless |
| NZ-amine-Starch Glucose Agar | Good | Heavy convoluted growth, 61. grayish yellowish brown to 65. brownish black; moderate aerial mycelia, white to 264. light gray | Greenish brown | 78. dark yellowish brown |
| Oatmeal Agar | Moderate | Flat waxy growth, 90. grayish yellow; moderate aerial mycelia, white | None | 90. grayish yellow |
| Tomato Paste Oatmeal Agar | Good | Flat waxy growth, 91. dark grayish yellow; trace of white aerial mycelia | None | — |
| Yeast Extract Malt Extract Agar | Good | Raised, waxy, convoluted colonies, 93. yellowish gray to 80. grayish yellowish brown; no aerial mycelia | Orange | 78. dark yellowish brown |

TABLE II

Micromorphology of *Actinomadura yumaense* NRRL 12515

| Medium | Aerial Mycelium and/or Sporiferous Structures | Spore Shape | Spore Size | Spore Surface |
|---|---|---|---|---|
| Czapek's Sucrose Agar | Aerial sporophores; branched, almost verticilate; carrying relatively short spiral chains of mature spores | Ovoid | 0.6–0.8 micron × 1.0–1.4 micron | Smooth |

TABLE III

Physiological Reactions of *Actinomadura yumaense* NRRL 12515

| Medium | Incubation Period | Amount of Growth | Physiological Reaction |
|---|---|---|---|
| Peptone-Iron Agar | 7 Days | Good | Slight browning |
| | 14 Days | Good | Slight browning |
| Tyrosine Agar | 7 Days | Moderate | No pigment |
| | 14 Days | Good | Yellowish pigment |
| Litmus Milk | 14 Days | Good | Good peptonization |
| | 28 Days | Good | Strong peptonization |
| Nutrient Gelatin | 14 Days | Good | Slight proteolysis |
| | 28 Days | Good | Total proteolysis |
| Nitrate Broth | 14 Days | Good | Very weak reduction |
| | 28 Days | Good | Moderate reduction |
| Adenine Agar | 14 Days | Good | No hydrolysis |
| | 21 Days | Good | No hydrolysis |
| Guanine Agar | 14 Days | Good | No hydrolysis |
| | 21 Days | Good | No hydrolysis |
| Hypoxanthine Agar | 14 Days | Good | Total hydrolysis |
| | 21 Days | Good | Total hydrolysis |
| Tyrosine Agar | 14 Days | Good | Strong hydrolysis |
| | 21 Days | Good | Strong hydrolysis |
| Xanthine Agar | 14 Days | Good | Moderate hydrolysis |
| | 21 Days | Good | Strong hydrolysis |
| NZ-amine with Soluble Starch and Glucose Agar (ATCC Med. No. 172) | 5 Days | Poor or no growth at 4° C., 10° C. and 55° C.; moderate growth at 25° C., 28° C. and 45° C.; good growth at 32° C. and 37° C. | |
| Urea Broth | 28 Days | Good | Decomposition variable |
| Esculin Broth | 14 Days | Good | Hydrolysis |
| | 28 Days | Good | Hydrolysis |
| Starch | 5 Days | Good | No Hydrolysis |

TABLE III-continued

Physiological Reactions of *Actinomadura yumaense* NRRL 12515

| Medium | Incubation Period | Amount of Growth | Physiological Reaction |
|---|---|---|---|
| Agar | 10 Days | Good | No Hydrolysis |

TABLE IV

Carbon Source Utilization of *Actinomadura yumaense* NRRL12515 on ISP-9 Carbohydrate Utilization Medium
Incubation: 28 days   Temperature: 28° C.

| Carbon Source | Utilization* |
|---|---|
| Adonitol | 0 |
| l-Arabinose | 0 |
| Dulcitol | 0 |
| Fructose | 1 |
| d-Galactose | 1 |
| d-Glucose | 3 |
| Glycerol | 3 |
| i-Inositol | 1 |
| Lactose | 0 |
| Maltose | 2 |
| d-Mannitol | 0 |
| d-Mannose | 1 |
| d-Melezitose | 1 |
| d-Melibiose | 0 |
| d-Raffinose | 0 |
| l-Rhamnose | 0 |
| Salicin | 0 |
| Sorbitol | 0 |
| Sucrose | 2 |
| d-Trehalose | 3 |
| d-Xylose | 0 |
| Negative Control | 0 |

*3 = Good utilization
2 = Fair utilization
1 = Poor utilization
0 = No utilization

TABLE V

Acid Production from Various Carbohydrates by *Actinomadura yumaense* NRRL 12515 on Gordon's Basal Inorganic Nitrogen Medium
Incubation: 28 days   Temperature: 28° C.

| Carbon Source | Acid Production 7 Days | Acid Production 28 Days |
|---|---|---|
| Adonitol | − | − |
| l-Arabinose | − | − |
| Dulcitol | − | − |
| Fructose | − | − |
| d-Galactose | − | + |
| d-Glucose | +++ | +++ |
| Glycerol | ++ | +++ |
| i-Inositol | − | + |
| Lactose | − | − |
| Maltose | − | +++ |
| d-Mannitol | − | − |
| d-Mannose | − | + |
| d-Melezitose | − | − |
| d-Melibiose | − | − |
| d-Raffinose | − | − |
| l-Rhamnose | − | − |
| Salicin | − | − |
| Sorbitol | − | − |
| Sucrose | ± | +++ |
| d-Trehalose | − | +++ |
| d-Xylose | − | − |
| Negative Control | − | − |

+++ = Strong positive response
++ = Moderate positve response
+ = Slight positive response
− = Negative response

TABLE VI

Utilization of Organic Acids by *Actinomadura yumaense* NRRL12515 on Gordon's Modification of Koser's Basal Agar (Koser's Citrate Agar)
Incubation: 28 days   Temperature: 28° C.

| Carbon Source | Utilization* |
|---|---|
| Acetate | + |
| Benzoate | − |
| Citrate | − |
| Lactate | − |
| Malate | + |
| Mucic Acid | − |
| Oxalate | − |
| Propionate | + |
| Pyruvate | + |
| Succinate | + |
| Tartrate | + |

+ = Positive response
− = Negative response

It is to be understood that for the production of these nematocidal agents, the present invention is not limited to this particular organism or to organisms fully answering the above growth and microscopic characteristics which are given for illustrative purposes only. In fact, it is desired and intended to include the use of mutants produced from this organism by various means such as exposure to X-radiation, ultraviolet radiation, nitrogen mustard, actinophages, and the like.

The present invention is further demonstrated by the examples set forth below. These examples are provided only by way of illustration and are not intended to be limiting on the invention.

EXAMPLE 1

Evaluation of test compositions for nematocidal activity using the free-living Hermaphroditic microbivorous nematode *Caenorhabditis elegans* II In the following tests, *C. elegans* is used to determine the nematocidal activity of the fermentation broth and the harvest mash prepared by the procedure of Example 5 following. This organism is also used to exaluate X 14868A and LL-C23024β to determine the nematocidal activity thereof.

In these tests, fermentation broth is the fermentation liquid and solids mixture taken before the solids, i.e., the harvest mash, is separated from the liquid. Harvest mash is the solids remaining after separation.

For evaluation of harvest mash, the harvest mash solids are dispersed 1:1 in distilled water. The fermentation broth is used as is and contains both liquid and solids.

In the present evaluations, *C. elegans* is maintained in a C. briggsae Maintenance Medium. The Maintenance Medium is commercially available from Grand Island Biological Company, Grand Island, N.Y., and has the following compositions:

| C. briggsae MAINTENANCE MEDIUM[1] | |
|---|---|
| Component | mg/L |
| INORGANIC SALTS | |
| $CaCl_2.2H_2O$ | 220.50 |
| $CuCl_2.2H_2O$ | 6.50 |
| $Fe(NH_4)_2(SO_4)_2.6H_2O$ | 58.80 |
| $KH_2PO_4$ | 1225.50 |
| KOH | (a) |
| $MnCl_2.4H_2O$ | 22.20 |
| $ZnCl_2$ | 10.20 |
| OTHER COMPONENTS | |
| N—Acetylglucosamine | 15.00 |

-continued

| C. briggsae MAINTENANCE MEDIUM[1] | |
|---|---|
| Component | mg/L |
| Adenosine-3'-(2')-phosphoric acid.$H_2O$ | 365.00 |
| Cytidine-3'-(2')-phosphoric acid | 323.00 |
| D-Glucose | 1315.00 |
| Glutathione, reduced | 204.00 |
| Guanosine-3'-(2')-$PO_4Na_2.H_2O$ | 363.00 |
| Magnesium citrate.$5H_2O$ (Dibasic) | 915.00 |
| Potassium citrate.$H_2O$ | 486.00 |
| DL-Thioctic acid | 3.75 |
| Thymine | 126.00 |
| Uridine-3'-(2')-phosphoric acid | 324.00 |
| AMINO ACIDS | |
| L-Alanine | 1395.00 |
| L-Arginine | 975.00 |
| L-Aspartic acid | 1620.00 |
| L-Cysteine HCl.$H_2O$ | 28.00 |
| L-Glutamate (Na).$H_2O$ | 550.00 |
| L-Glutamine | 1463.00 |
| Glycine | 722.00 |
| L-Histidine | 283.00 |
| L-Isoleucine | 861.00 |
| L-Leucine | 1439.00 |
| L-Lysine HCl | 1283.00 |
| L-Methionine | 389.00 |
| L-Phenylalanine | 803.00 |
| L-Proline | 653.00 |
| L-Serine | 788.00 |
| L-Threonine | 717.00 |
| L-Tryptophan | 184.00 |
| L-Tyrosine | 272.00 |
| L-Valine | 1020.00 |
| VITAMINS | |
| p-aminobenzoic acid | 7.50 |
| Biotin | 3.75 |
| Choline dihydrogen citrate | 88.50 |
| Cyanocobalamine ($B^{12}$) | 3.75 |
| Folinate (Ca) | 3.75 |
| Myo-inositol | 64.50 |
| Niacin | 7.50 |
| Niacinamide | 7.50 |
| Pantethine | 3.75 |
| Pantothenate (Ca) | 7.50 |
| Pterolyglutamic acid | 7.50 |
| Pyridoxal phosphate | 3.75 |
| Pyridoxamine 2HCl | 3.75 |
| Pyridoxine HCl | 7.50 |
| Riboflavin-5'-$PO_4$(Na).$2H_2O$ | 7.50 |
| Thiamine HCl | 7.50 |

References:
[1]Hansen, E. L., Proc. Soc. Exp. Bio. & Med. 121:390–393 (1966).
Remarks:
(a)As needed for adjustment to pH 5.9 + 0.1

A well plate having a series of small wells is used for the evaluations. Twenty-five ml of fermentation broth, 1:1 water/harvest mash suspension, or an aqueous/acetone solution of X-14868A or LL-23024β containing from 31.25 to 500 ppm of test compound, is asceptically deposited in separate wells. To each well is then added 25 ml of the C. elegans maintenance medium containing 10–20 adult worms plus larvae of various ages plus eggs. The plates are then placed in a hood and examined at 48 hours post-inoculation to assess the speed and degree of nematocidal activity of the test compositions. Data obtained are reported below. Where activity is observed for the fermentation broth, said broth is further diluted to provide a 1:4 broth to C. elegans ratio.

TABLE 7

| Composition | Concentration ppm or Dilution | Nematocidal Activity at 48 hours |
|---|---|---|
| Fermentation Broth | D = 1:1 | 8 (no motility) |
| | D = 1:4 | 8 |

TABLE 7-continued

| Composition | Concentration ppm or Dilution | Nematocidal Activity at 48 hours |
|---|---|---|
| Harvest Mash X 14868A | 500 ppm | 7 |
| | 250 ppm | 7 |
| | 125 ppm | 7 |
| | 62.5 ppm | 6 |
| | 31.25 ppm | 0 |
| LL-23024 β | 500 ppm | 7 |
| | 250 ppm | 0 |

The activity legend employed in these evaluations is as follows:

Activity Legend

8 = No Motility (Apparent Death)
7 = Markedly Reduced Motility
6 = Reduced Motility
0 = Normal Motility for Species

EXAMPLE 2

Evaluation of X 14868A as a nematocidal agent against infective larvae** of ruminant nematodes Evaluation of X 14868A as a nematocidal agent against the infective larvae of ruminant nematodes: *Haemonhmus contortus, Ostertagia circumcincta, Trichostrongylus axei, T. Colubriformis;* and against the vinegar eel worm, *Turbatrix aceti* was determined using the above-mentioned nematode species were substituted for *C. elegans.*

Data obtained are reported in the Table below.
**Third Stage Sheathed Larvae

TABLE VIII

| In Vitro[a] Concentration of X14868A ppm | Activity Against (at 48 Hours) | | | | |
|---|---|---|---|---|---|
| | H Contort. | O. Circum. | T. Axei | T. Colub. | T. Aceti |
| 500 | 8 | 8[b] | 8[b] | 8 | 6 |
| 250 | 7 | 8[b] | 8[b] | 7 | 6 |
| 125 | 7 | 7 | 7 | 6 | 6 |
| 625 | 7 | 6 | 7 | 6 | 6 |
| 31.25 | 6 | 6 | 0 | 6 | 6 |
| 0 (Control) | 0 | 0 | 0 | 0 | 0 |

[a]Conducted in 96-well tissue culture plates, X14868A prepared in double-distilled water: 25 μl of X14868A solution and 25 μl of nematode culture were added per well.
Activity Legend:
8 = No Motility (Apparent Death)
7 = Markedly Reduced Motility
6 = Reduced Motility
0 = Normal Motility for Species
[b]Within 24 hours

EXAMPLE 3

Evaluation of nematocidal activity of antibiotic X 14868A against *Nematospiroides dubius* and *Aspicularis tetraptera* in mice In the following tests, Swiss-Webster female white mice are infected with *Namatospiroides dubius* and *Aspicularis tetraptera* and held for three weeks to permit the infections to mature.

After the holding period, the mice are randomly divided into groups of four, and the groups placed in separate cages. Medicated feeds containing from about 31.25 ppm to 4,000 ppm of test compound are then offered ad lubitum to the mice for one week. Water is also provided ad libitum throughout the test period. During the treatment period, the mouse droppings are examined to determine whether worms are being passed. All treatment groups were found to be passing worms, thus indicating nematocidal activity at all compound concentrations against both nematodes. At the end of the one-week medicated feed treatment, the mice are necropsied, and the contents of the intestinal tracts thereof examined for worms. Data obtained are reported below as percent reduction of worms as compared with infected, unmedicated controls.

In these tests, crude fermentation broths obtained before harvest of the mash, as described in Example 5 below, and containing from 1,000 ppm to 4,000 ppm of the nematocidal antibiotic were evaluated. Also evaluated was mouse feed treated with from 31.25 ppm to 500 ppm of X 14868A dissolved in an acetone/water 1:1 mixture.

| Test Composition | Dietary Conc. ppm | Activity (% Reduction)*** Against | |
|---|---|---|---|
| | | N. dubius | A. tetraptera |
| *Fermenta- | 4,000 | 73 | — |
| tion Broth | 2,000 | 44 | 53 |
| with X 14868A | 1,000 | 65 | 33 |
| X 14868A | 500 | 70 | SA** |
| | 250 | 63 | SA |
| | 125 | 61 | SA |
| | 62.5 | 29 | SA |
| | 31.25 | 32 | SA |

*Amount of X 14868A undetermined
**Slight activity: Increased number of pinworms recovered in fecal examination
***Compared to infected unmedicated controls Cultivation of *Actinomadura yumaense* may be carried out in a wide variety of liquid culture media. Media which are useful for the production of these novel antibacterial agents include an assimilable source of carbon such as starch, sugar, molasses, glycerol, etc., an assimilable source of nitrogen such as protein, protein hydrolysate, polypeptides, amino acids, corn steep liquor, etc., and inorganic anions and cations, such as potassium, sodium, ammonium, calcium, sulfate, carbonate, phosphate, chloride, etc. Trace elements such as boron, molybdenum, copper, etc., are supplied as impurities of other constituents of the media. Aeration in tanks and bottles is provided by forcing sterile air through or onto the surface of the fermenting medium. Further agitation in tanks is provided by a mechanical impeller. An antifoaming agent such as lard oil may be added as needed.

Inoculum Preparation

Shaker flask inoculum of *Actinomadura yumaense* NRRL 12515 is prepared by inoculating 100 ml of sterile liquid medium in 500 ml flasks with scrapings or washings of spores from an agar slant of the culture. The following is an example of a suitable medium:
 Beef extract—0.3%
 Bacto tryptone—0.5%
 Glucose—1.0%
 Yeast extract—0.5%
 Bacto agar—0.15%
 Water, qs—100.0%

The flasks are incubated at a temperature of 25°–30° C., preferably 32° C., and agitated vigorously on a rotary shaker for 24–48 hours.

A 100 ml. portion of the above flask inoculum is then used to inoculate one liter of the same sterile medium in a 2 liter bottle. This inoculum is aerated with sterile air while growth is continued for 24–48 hours. This inoculum is used to inoculate tank fermentors.

Tank Fermentation

For the production of X 14868A and LL-C23024β in tank fermentors the following sterilized medium may be used:
 Dextrose—1.5%
 Glycerol—1.5%
 Soy flour—1.5%
 Calcium carbonate—0.1%
 Sodium chloride—0.3%
 Water, qs—100%
 pH adjusted to 7.0 with 6N sodium hydroxide Each tank is inoculated with 3–10% of inoculum prepared as described above. Aeration is supplied at the rate of 0.5 to 2.0 liter of sterile air per liter of broth per minute and the fermenting medium is agitated by an impeller driven at 200–400 rpm. The temperature is maintained at 25°–35° C., preferably at 32° C. The fermentation is usually continued for 100–150 hours, at which time the mash is harvested.

EXAMPLE 4

Inoculum Preparation

A typical medium used to grow the primary inoculum is prepared according to the following formula:
 Beef extract—0.3%
 Bacto tryptone—0.5%
 Glucose—1.0%
 Yeast extract—0.5%
 Bacto agar—0.15%
 Water, qs—100%

Washed or scraped spores from an agar slant of *Actinomadura yumaense* NRRL 23515 are used to inoculate a 500 ml. flask containing 100 ml. of the above sterilized medium. The flask is placed on a rotary shaker and agitated vigorously for 24 hours at 32° C. The resulting flask inoculum (100 ml.) is used to inoculate one liter of the same sterile medium in a 2 liter bottle. This inoculum is aerated with sterile air while growth is continued for 24 hours at 28° C.

EXAMPLE 5

Fermentation

A fermentation medium is prepared according to the following formula:
 Dextrose—1.5%
 Glycerol—1.5%
 Soy flour—1.5%
 Calcium carbonate—0.1%
 Sodium chloride—0.3%
 Water, qs—100%

The pH is adjusted to 7.0 with 6N sodium hydroxide and the medium is sterilized. A one liter portion of inoculum prepared as described in Example 4 is used to inoculate 25 liters of the above medium in a 30 liter fermentor. Sterile aeration is supplied to the mash. The mash is agitated by an impeller driven at 400 rpm. Fermentation is carried out at 32° C. for 114 hours at which time the mesh is harvested.

EXAMPLE 6

Isolation of X 14868A

A total of 52 liters of harvest mash, prepared from fermentations conducted as described in Example 2 is mixed with an equal volume of methylene chloride. The aqueous phase is separated and stirred with 52 liters of methylene chloride. The organic phase is separated and concentrated in vacuo to 115 g. of a syrupy residue.

A glass column (4 cm. diameter) is packed to a height of 84 cm. with silica gel. A 23 g portion of the above residue is dissolved in 25 ml. of methylene chloride and allowed to seep into the column. The column is developed in succession with 2 liters of methylene chloride, 2 liters of methylene chloride:ethyl acetate (1:1). Fractions of 50 ml. each are collected and checked for the presence of antibacterial activity by bioautography against *Bacillus subtilis* Stansly R-78, grown on nutrient agar at pH 6.0. Fractions 85–99 are combined, desolventized and freeze-dried in t-butanol, giving 2.217 g. of solid.

A 700 mg. portion of this solid is dissolved in 100 ml. of diethyl ether. This solution is shaken with 100 ml. of water and the pH adjusted to 2.5 with 0.1N hydrochloric acid. The ether phase is separated, washed with five 50 ml. portions of water, added to 100 ml. of water and the pH adjusted to 9.0 with 0.1N sodium hydroxide. The ether phase is again separated and washed with five 50 ml. portions of water. The ether solution is then dried over sodium sulfate, filtered and concentrated to a residue in vacuo. This residue is dissolved in 12 ml. of ether, 30 ml. of hexane are added and the solution is allowed to evaporate slowly at 4° C. for 16 hours. The crystals are collected, washed with cold hexane and air dried, giving 402 mg. of X 14868A.

$^{13}$C. NMR spectra of X 14868A and LL-C23024$\beta$ were obtained in deuterated chloroform at a field strength of 20 MHz. The peaks with their respective chemical shifts and the number of carbons by interpretation are listed in Table VIII. Peaks were observed for chloroform at 76.5, 77.0 and 77.5.

The carbons with chemical shifts of 107.5, 97.7, 97.3, 84.9 and 84.4 ppm for X 14868A gave negative peaks when run at 62.89 MHz under inversion recovery conditions (180-t-90) with t=0.8 sec.

TABLE IX $^{13}$C NMR Spectra (20 MNz) of X 14868A and LL-C23024$\beta$ in CDCl$_3$, Internal Reference TMS

| Chemical Shift, δ (ppm) | | Number of Carbons | |
|---|---|---|---|
| X 14868A | LL-C23024$\beta$ | X 14868A | LL-C23024$\beta$ |
| 10.5 | 10.5 | 1 | 1 |
| 11.0 | 11.0 | 1 | 1 |
| 12.0 | 12.2 | 1 | 1 |
| 17.0 | 17.0 | 1 | 1 |
| 17.7 | 17.7 | 1 | 1 |
| 17.9 | 17.9 | 1 | 1 |
| 22.4 | 22.3 | 1 | 1 |
| 26.0 | 26.1 | 1 | 1 |
| 26.8 | 26.8 | 1 | 1 |
| 27.6 | 27.6 | 1 | 1 |
| 30.3 | 30.2 | 1 | 1 |
| 32.0 | 32.0 | 1 | 1 |
| 33.3 | 33.3 | 3 | 1 |
| 33.7 | 33.7 | 2 | 2 |
| — | 33.8 | — | 2 |
| 36.5 | 36.5 | 1 | 1 |
| 36.8 | 36.8 | 1 | 1 |
| 39.0 | 39.0 | 1 | 1 |
| 39.9 | 39.9 | 1 | 1 |

TABLE IX-continued $^{13}$C NMR Spectra (20 MNz) of X 14868A and LL-C23024$\beta$ in CDCl$_3$, Internal Reference TMS

| Chemical Shift, δ (ppm) | | Number of Carbons | |
|---|---|---|---|
| X 14868A | LL-C23024$\beta$ | X 14868A | LL-C23024$\beta$ |
| 45.5 | 45.5 | 2 | 2 |
| 57.0 | 57.1 | 1 | 1 |
| 59.5 | 59.1 | 1 | 1 |
| 60.5 | — | 1 | — |
| 60.7 | 60.7 | 1 | 1 |
| 67.5 | 66.9 | 2 | 1 |
| — | 67.6 | — | 1 |
| 70.2 | 70.2 | 1 | 1 |
| 71.3 | 71.3 | 1 | 1 |
| 72.9 | 72.9 | 1 | 1 |
| — | 74.9 | — | 1 |
| 75.3 | 75.1 | 1 | 1 |
| 79.9 | 79.9 | 1 | 1 |
| 80.8 | 80.8 | 1 | 1 |
| 82.0 | 82.1 | 1 | 1 |
| 82.2 | — | 1 | — |
| 84.5 | 84.5 | 1 | 1 |
| 84.6 | 84.7 | 1 | 1 |
| 85.6 | 85.6 | 2 | 1 |
| 86.9 | 86.9 | 1 | 1 |
| 95.8 | 95.8 | 1 | 1 |
| 96.9 | 96.9 | 1 | 1 |
| 97.6 | 97.7 | 1 | 1 |
| 107.4 | 107.5 | 1 | 1 |
| 178.9 | 179.2 | 1 | 1 |
| | Total Carbons | 47 | 46 |

EXAMPLE 7

Isolation of LL-C23024$\beta$

A total of 100 liters of harvest mash, prepared from fermentations conducted as described in Example 5 is adjusted to pH 4.0 using hydrochloric acid and then stirred with an equal volume of methylene chloride. This mixture is filtered through diatomaceous earth and the methylene chloride phase is separated and concentrated in vacuo to an oily residue. This residue is redissolved in 2 liters of methylene chloride, sodium acetate and sodium sulfate are added until the pH is 5.5 and the mixture is filtered.

A glass column with a diameter of 7 cm. is packed to a height of 91 cm. with silica gel. The above 2 liters of pH 5.5 filtrate is allowed to seep into the column which is then developed first with 3 liters of methylene chloride and then with methylene chloride:ethyl acetate (1:1). A total of 126 fractions of 80 ml. of each are collected. The column is then developed with ethyl acetate:ethanol (7:3) giving an additional 87 fractions. Of this total of 213 fractions, the fractions 177–213 are combined and concentrated in vacuo, giving 66.82 g. of solid.

A glass column with a diameter of 2 inches is packed to a height of 34 inches with a gel prepared by allowing an hydroxypropylated dextran (Sephadex ® LH20) to swell in hexane:methylene chloride:methanol (1000:500:100). A 3.0 g. portion of the above solid (prepared from fractions 177–213) is dissolved by the sequential additional of 10 ml. of methylene chloride, one ml. of methanol and 10 ml. of hexane. This solution is allowed to seep into the column which is then developed with the system hexane:methylene chloride:methanol (1000:500:100). Twenty-three fractions with a volume of 31 ml. each are collected, followed by fractions 24–100 with a volume of 17 ml. each. The fractions are checked for antibiotic activity by thin layer chromatography and by bioautography.

Fractions 17–26 are combined and concentrated in vacuo, giving 1269 mg. of LL-C23024β as an off-white solid. This solid is crystallized as described for X 14868A in Example 5, giving a solid having the following characteristics:

Empirical formula: $C_{46}H_{78}O_{17}$.
Elemental analysis: C, 61.55; H, 8.79%

$$[\alpha]_D^{25} = +32° \pm 2 \text{ (0.495\%, methanol)}$$
$$+46° \pm 2 \text{ (0.440\%, chloroform)}$$

Molecular weight by field desorption mass spectoscopy 902.

Melting point: 171°–173° C.

An IR spectrum (KBr) as shown in FIG. 1 of copending Ser. No. 372,784.

A $^{13}C$ NMR spectrum (in $CDCl_3$ at 20 MHz) as shown in FIG. II of copending Ser. No. 372,784.

A $^1H$ NMR spectrum (in $CDCl_3$ at 80 MHz) as shown in FIG. III of copending Ser. No. 372,784.

The significant $^{13}C$-NMR absorptions are shown in Table I of copending Ser. No. 372,784.

EXAMPLE 8

Potassium Complex of X 14868A

A 170 mg. portion of X 14868A is dissolved in a solution of 125 ml. of diethyl ether in 125 ml. of low boiling petroleum ether. This solution is transferred to a separatory funnel containing 125 ml. of water, which has been made acid by the addition of 5 ml. of 0.1N hydrochloric acid. The mixture is shaken, then allowed to settle and the aqueous phase discarded. The organic phase is washed with four 100 ml. portions of water, then placed over 100 ml. of water and adjusted to pH 9.8 with 2N potassium hydroxide. The mixture is shaken and after settling, the aqueous phase is discarded. The organic phase is washed with four 100 ml. portions of water and then concentrated in vacuo to a residue. This residue is dissolved in t-butanol and then lyophilized, giving 99 mg. of the desired product, having the following characteristics:

Elemental analysis: C, 58.28; H, 8.45; K, 3.36%.

Molecular weight by mass field desorption spectrometry: 955.

EXAMPLE 9

Rubidium Complex of X 14868A

A 400 mg. portion of X 14868A is dissolved in a mixture of 200 ml. of diethyl ether and 200 ml. of hexane. This solution is placed over 125 ml. of water and sufficient dilute hydrochloric acid is added to alter the pH to 2.5. The mixture is shaken, then allowed to settle. The aqueous phase is discarded and the organic phase is again washed with dilute acid. The separated organic phase is then washed several times with equal volumes of water and then a fresh layer of water is placed below the organic layer. A solution of 4.0 g. of rubidium hydroxide in 75 ml. of water is added dropwise until the aqueous phase reaches a pH of 10.1, after shaking and settling. The organic layer is separated, washed once with 150 ml. of water and then concentrated in vacuo until a crystalline solid starts to form. The concentrate is then allowed to stand for 2 hours and the crystalline solid collected, washed with hexane and dried, giving 240 mg. of the desired product having the following characteristics:

Elemental analysis: C, 56.74; H, 7.97; Rb, 9.58%.

Molecular weight by field desorption mass spectroscopy: 1001.

Melting point: 175°–177° C.

I claim:

1. A method of controlling nematodes in warm-blooded animals infested with nematodes and in soil containing the nematodes by introducing orally into the animals or applying to nematodes in nematode-infested soil, a nematocidally effective amount of a compound

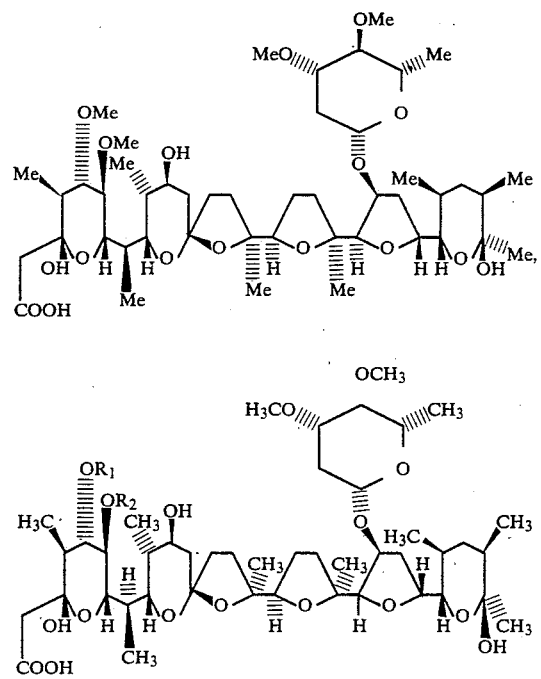

wherein $R_1$ is H or $CH_3$, $R_2$ is H or $CH_3$ and $R_1$ does not equal $R_2$ or pharmaceutically acceptable salts of the compounds, mixtures of the compounds or salts, or fermentation broths or harvest mash solids from which the nematocidal antibiotics are obtained.

2. A method according to claim 1 for controlling nematodes in warm-blooded animals by orally administering to companion or farm animals a composition comprising an edible carrier containing about 0.5 ppm to 30 ppm of the nematocidal compound or mixture of nematocidal compounds.

3. A method for the control of nematode infestations in warm-blooded animals comprising orally administering to nematode-infested animals an animal feedstuff containing a nematocidally effective amount in the range of 0.5 ppm to 30 ppm, a compound

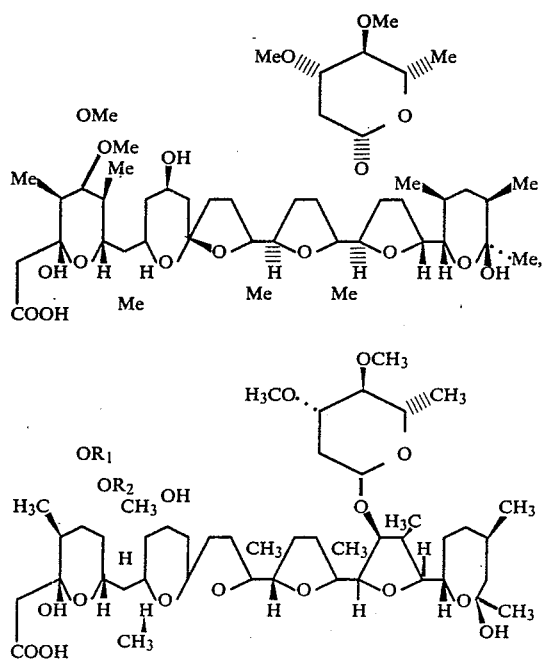

wherein $R_1$ is H or $CH_3$, $R_2$ is H or $CH_3$ and $R_1$ does not equal $R_2$ or the pharmaceutically acceptable salts or mixtures thereof or a fermentation harvest mash containing the compound, in an animal feed.

4. A method for controlling nematodes in laboratory animals infested with nematodes by introducing orally into the animals an animal feed composition comprising an edible feed and about 31.25 ppm to 500 ppm of a compound

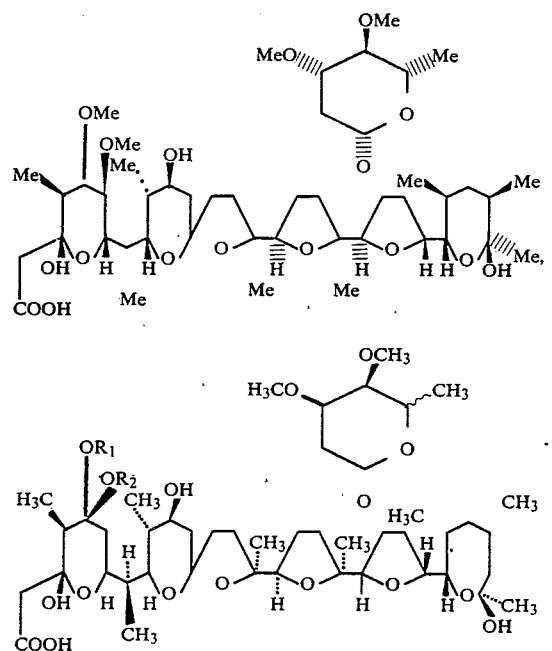

wherein $R_1$ is H or $CH_3$, $R_2$ is H or $CH_3$ and $R_1$ does not equal $R_2$ or the pharmaceutically acceptable salts or mixtures thereof or a fermentation harvest mash containing the compound.

5. A method of eradicating parasitic nematodes in an animal infested with nematodes by introducing orally into its alimentary tract a composition comprising an animal feed containing from about 1 ppm to 15 ppm of an antibiotic

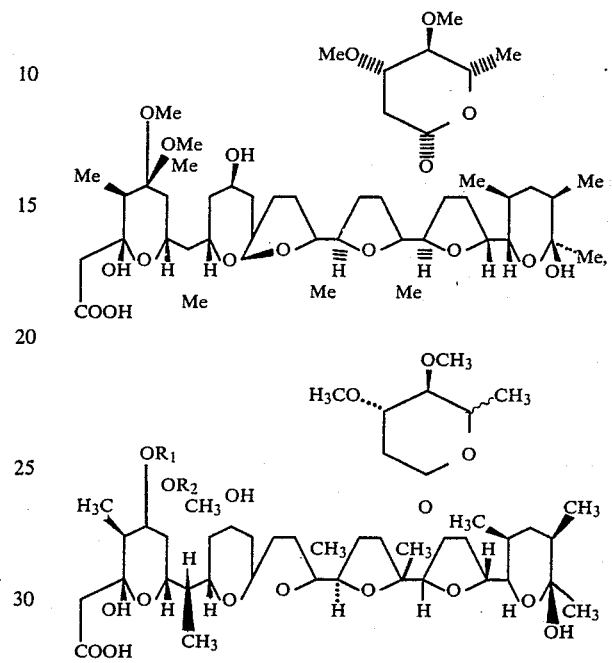

wherein $R_1$ is H or $CH_3$, $R_2$ is H or $CH_3$ and $R_1$ does not equal $R_2$ or the pharmaceutically acceptable salts or mixtures thereof or a fermentation harvest mash containing the compound.

6. A method of controlling nematodes in soil comprising applying to nematodes in a nematode infested soil a nematocidally effective amount of a compound

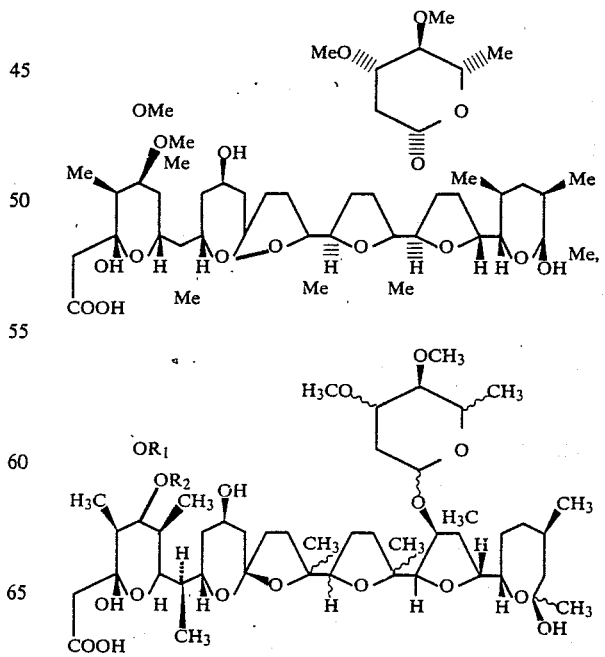

wherein $R_1$ is H or $CH_3$, $R_2$ is H or $CH_3$ and $R_1$ does not equal $R_2$ or the pharmaceutically acceptable salts or mixtures thereof or a fermentation harvest mash containing the compound.

7. A method according to claim 6 wherein the compound is

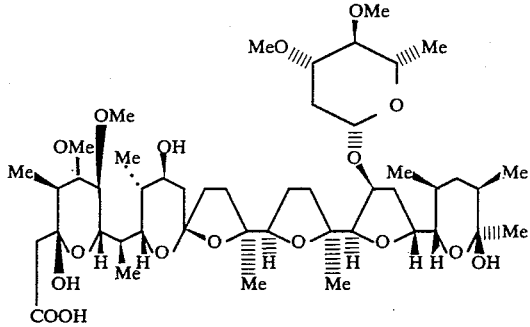

and is applied at the rate of from 0.125 kg/ha to about 4.0 kg/ha.

8. A method according to claim 6 wherein the compound is

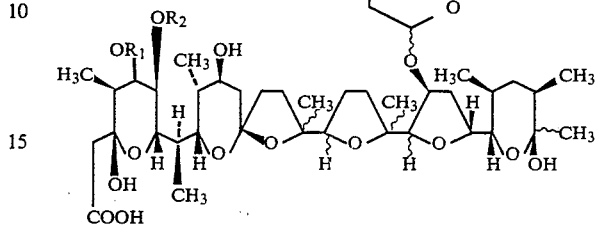

wherein $R_1$ is H or $CH_3$, $R_2$ is H or $CH_3$ and $R_1$ does not equal $R_2$ and is applied at the rate of from 0.125 kg/ha to about 4.0 kg/ha.

* * * * *